(12) United States Patent
Huang et al.

(10) Patent No.: US 7,629,438 B2
(45) Date of Patent: Dec. 8, 2009

(54) GROUP OF SYNTHETIC ANTIMICROBIAL PEPTIDES

(76) Inventors: Qingshan Huang, Room B, 3/F. No. 501 Jingang Road, Pudong New District, Shanghai (CN) 201206; Guodong Li, Room B, 3/F. No. 501 Jingang Road, Pudong New District, Shanghai (CN) 201206

( * ) Notice: Subject to any disclaimer, the term of this patent is extended or adjusted under 35 U.S.C. 154(b) by 461 days.

(21) Appl. No.: 10/526,267

(22) PCT Filed: Jul. 1, 2003

(86) PCT No.: PCT/CN03/00522

§ 371 (c)(1), (2), (4) Date: Mar. 23, 2006

(87) PCT Pub. No.: WO2004/020461

PCT Pub. Date: Mar. 11, 2004

(65) Prior Publication Data

US 2008/0070279 A1    Mar. 20, 2008

(30) Foreign Application Priority Data

Sep. 2, 2002 (CN) .............................. 02 1 36766

(51) Int. Cl.
*A61K 38/16* (2006.01)
*A61K 38/00* (2006.01)
*A01N 37/00* (2006.01)

(52) U.S. Cl. ............................ 530/326; 530/334; 514/2
(58) Field of Classification Search ................. 530/326, 530/334; 514/2
See application file for complete search history.

(56) References Cited

U.S. PATENT DOCUMENTS 6,071,879 A    6/2000   Pereira
6,800,727 B2 *  10/2004   Hahm et al. ................. 530/300

FOREIGN PATENT DOCUMENTS

WO    WO 95/03325 A1    2/1995
WO    WO 00/09553       2/2000
WO    WO 00/09553 A2    2/2000

OTHER PUBLICATIONS

Broth, W.B. et al., Effects of Synthetic Cecropin Analogs on in Vitro Growth of *Acholeplasma laidlawii*. Antimicrobial Agents and Chemotherapy 45(6): 1894-1895, 2001.
International Search Report from PCT/CNO3/00522, mailed Nov. 13, 2003.
Nakajima, Y. et al., Interaction between Liposomes and Sarcotoxin IA, a Potent Antibacterial Protein of *Sarcophaga peregrina* (Flesh Fly). The Journal of Biological Chemsitry 262(4): 1665-1669, 1987.
Zasloff, M. Antimicrobial peptides of multicellular organisms. Nature 415: 389-395, 2002.
Borth, Wayne B. et al., "Effects of synthetic cecropin analogs on in vitro growth of *Acholeplasma laidlawii*," *Antimicrobial Agents and Chemotherapy*, vol. 45, No. 6, pp. 1894-1895, Jun. 2001.
Deslouches, Berthony et al., "De novo generation of cationic antimicrobial peptides; influence of length and tryptopham substitution on antimicrobial activity," *Antimicrobial Agent and Chemotherapy*, vol. 49, No. 1, pp. 316-322, Jan. 2005.
Hong, Sung Yu et al., "The effect of charge increase on the specificity and activity of a short antimicrobial peptide," *Peptides*, 22, pp. 1669-1674, 2001.
Nakajima, Yuki et al., "Interaction between liposomes and sarcotoxin IA, a potent antibacterial protein of *Sarcohaga peregrina* (Flesh Fly)," *The Journal of Biological Chemistry*, vol. 262, No. 4, pp. 1665-1669, Feb. 5, 1987.
Scott, Monish et al., "Biological properties of structurally related alpha-Helical cationic antimicrobial peptides," *Infection and Immunity*, pp. 2005-2009, Apr. 1999.
Zasloff, Michael, "Antimicrobial peptides of multicellular organisms," *Nature*, vol. 415, pp. 389-395, Jan. 24, 2002.

* cited by examiner

*Primary Examiner*—Maryam Monshipouri
*Assistant Examiner*—Marsha M Tsay
(74) *Attorney, Agent, or Firm*—Wolf, Greenfield & Sacks, P.C.

(57) ABSTRACT

A group of new synthetic antimicrobial peptides are disclosed, which demonstrate stronger bactericidal activity than native antimicrobial peptides. The present synthetic antimicrobial peptides can be produced by solid-phase chemical synthesis or gene expression and be used to prepare the medicines for treating the diseases induced by bacteria, viruses and fungi, as well as the anticancer drugs.

6 Claims, 1 Drawing Sheet

SEQUENCE LISTING

<160> NUMBER OF SEQ ID NOS: 54

<210> SEQ ID NO 1
<211> LENGTH: 19
<212> TYPE: PRT
<213> ORGANISM: Artificial Sequence
<220> FEATURE:
<223> OTHER INFORMATION: Synthetic Polypeptide
    220>
<221> NAME/KEY: MISC_FEATURE
<222> LOCATION: (12,16)
<223> OTHER INFORMATION: Xaa=Lys or Arg
<220> FEATURE:
<221> NAME/KEY: misc_feature
<222> LOCATION: (13,17)
<223> OTHER INFORMATION: Xaa=Gly or Ala or Val or Leu or Ile or Phe
<220> FEATURE:
<221> NAME/KEY: misc_feature
<222> LOCATION: (14,18)
<223> OTHER INFORMATION: Xaa=Gly or Ala or Val or Leu or Ile or Phe
<220> FEATURE:
<221> NAME/KEY: misc_feature
<222> LOCATION: (15,19)
<223> OTHER INFORMATION: Xaa=Lys or Arg

<400> SEQUENCE: 1

Arg Phe Arg Leu Val Arg Arg Ile Val Leu Ala Xaa Xaa Xaa Xaa
                 5                  10                  15

Xaa Xaa Xaa Xaa

<210> SEQ ID NO 2
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 2

Arg Phe Arg Leu Val Arg Arg Ile Val Leu Ala Xaa Xaa Xaa Xaa
                 5                  10                  15

Xaa Xaa Xaa Xaa Xaa Xaa Xaa Xaa
20

<210> SEQ ID NO 3
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:

-continued

```
<221> NAME/KEY: MISC_FEATURE
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 3

Arg Phe Lys Leu Val Arg Arg Ile Val Leu Ala Xaa Xaa Xaa Xaa
                 5                  10                  15

Xaa Xaa Xaa Xaa

<210> SEQ ID NO 4
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 4

Arg Phe Lys Leu Val Arg Arg Ile Val Leu Ala Xaa Xaa Xaa Xaa
                 5                  10                  15

Xaa Xaa Xaa Xaa Xaa Xaa Xaa Xaa
            20

<210> SEQ ID NO 5
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<220> FEATURE:
<221> NAME/KEY: MISC_FEATURE
<222> LOCATION: (12,16)
<223> OTHER INFORMATION: Xaa=Lys or Arg
<220> FEATURE:
<221> NAME/KEY: MISC_FEATURE
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 5
```

Arg Phe Lys Leu Val Lys Arg Ile Val Leu Ala Xaa Xaa Xaa Xaa
                5                   10                  15

Xaa Xaa Xaa Xaa

<210> SEQ ID NO 6
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 6

Arg Phe Lys Leu Val Lys Arg Ile Val Leu Ala Xaa Xaa Xaa Xaa
                5                   10                  15

Xaa Xaa Xaa Xaa Xaa Xaa Xaa Xaa
20

<210> SEQ ID NO 7
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:
<221> NAME/KEY: MISC_FEATURE
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 7

Arg Phe Lys Leu Val Lys Lys Ile Val Leu Ala Xaa Xaa Xaa Xaa
                5                   10                  15

Xaa Xaa Xaa Xaa

<210> SEQ ID NO 8
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg

```
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 8

Arg Phe Lys Leu Val Lys Lys Ile Val Leu Ala Xaa Xaa Xaa Xaa
                 5                  10                  15

Xaa Xaa Xaa Xaa Xaa Xaa Xaa Xaa
20

<210> SEQ ID NO 9
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:
<221> NAME/KEY: MISC_FEATURE
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 9

Lys Phe Lys Leu Val Lys Lys Ile Val Leu Ala Xaa Xaa Xaa Xaa
                 5                  10                  15

Xaa Xaa Xaa Xaa

<210> SEQ ID NO 10
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 10

Lys Phe Lys Leu Val Lys Lys Ile Val Leu Ala Xaa Xaa Xaa Xaa
```

```
                    5                   10                  15
Xaa Xaa Xaa Xaa Xaa Xaa Xaa Xaa
 20

<210> SEQ ID NO 11
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:
<221> NAME/KEY: MISC_FEATURE
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 11

Arg Phe Arg Leu Phe Arg Arg Ile Leu Val Gly Xaa Xaa Xaa Xaa
                    5                   10                  15

Xaa Xaa Xaa Xaa

<210> SEQ ID NO 12
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 12

Arg Phe Arg Leu Phe Arg Arg Ile Leu Val Gly Xaa Xaa Xaa Xaa
                    5                   10                  15

Xaa Xaa Xaa Xaa Xaa Xaa Xaa Xaa
 20

<210> SEQ ID NO 13
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
```

```
<220> FEATURE:
<221> NAME/KEY: MISC_FEATURE
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 13

Arg Phe Lys Leu Phe Arg Arg Ile Leu Val Gly Xaa Xaa Xaa Xaa
                5                   10                  15

Xaa Xaa Xaa Xaa

<210> SEQ ID NO 14
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 14

Arg Phe Lys Leu Phe Arg Arg Ile Leu Val Gly Xaa Xaa Xaa Xaa
                5                   10                  15

Xaa Xaa Xaa Xaa Xaa Xaa Xaa Xaa
20

<210> SEQ ID NO 15
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:
<221> NAME/KEY: MISC_FEATURE
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 15

Arg Phe Lys Leu Phe Lys Arg Ile Leu Val Gly Xaa Xaa Xaa Xaa
```

```
                5                  10                  15
Xaa Xaa Xaa Xaa

<210> SEQ ID NO 16
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 16

Arg Phe Lys Leu Phe Lys Arg Ile Leu Val Gly Xaa Xaa Xaa Xaa
                5                  10                  15

Xaa Xaa Xaa Xaa Xaa Xaa Xaa Xaa
                20

<210> SEQ ID NO 17
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:
<221> NAME/KEY: MISC_FEATURE
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 17

Arg Phe Lys Leu Phe Lys Lys Ile Leu Val Gly Xaa Xaa Xaa Xaa
                5                  10                  15

Xaa Xaa Xaa Xaa

<210> SEQ ID NO 18
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
```

```
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 18

Arg Phe Lys Leu Phe Lys Lys Ile Leu Val Gly Xaa Xaa Xaa Xaa
                 5                  10                  15

Xaa Xaa Xaa Xaa Xaa Xaa Xaa Xaa
            20

<210> SEQ ID NO 19
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:
<221> NAME/KEY: MISC_FEATURE
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 19

Lys Phe Lys Leu Phe Lys Lys Ile Leu Val Gly Xaa Xaa Xaa Xaa
                 5                  10                  15

Xaa Xaa Xaa Xaa

<210> SEQ ID NO 20
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 20

Lys Phe Lys Leu Phe Lys Lys Ile Leu Val Gly Xaa Xaa Xaa Xaa
                 5                  10                  15
```

```
Xaa Xaa Xaa Xaa Xaa Xaa Xaa Xaa
            20

<210> SEQ ID NO 21
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:
<221> NAME/KEY: MISC_FEATURE
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 21

Arg Phe Arg Gly Val Arg Arg Ile Leu Val Gly Xaa Xaa Xaa Xaa
                 5                  10                  15

Xaa Xaa Xaa Xaa

<210> SEQ ID NO 22
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 22

Arg Phe Arg Gly Val Arg Arg Ile Leu Val Gly Xaa Xaa Xaa Xaa
                 5                  10                  15

Xaa Xaa Xaa Xaa Xaa Xaa Xaa Xaa
            20

<210> SEQ ID NO 23
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:
```

```
<221> NAME/KEY: MISC_FEATURE
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 23

Arg Phe Arg Gly Val Lys Arg Ile Leu Val Gly Xaa Xaa Xaa Xaa
                 5                  10                  15

Xaa Xaa Xaa Xaa

<210> SEQ ID NO 24
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 24

Arg Phe Arg Gly Val Lys Arg Ile Leu Val Gly Xaa Xaa Xaa Xaa
                 5                  10                  15

Xaa Xaa Xaa Xaa Xaa Xaa Xaa Xaa
                 20

<210> SEQ ID NO 25
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:
<221> NAME/KEY: MISC_FEATURE
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 25

Arg Phe Arg Gly Val Lys Lys Ile Leu Val Gly Xaa Xaa Xaa Xaa
                 5                  10                  15
```

Xaa Xaa Xaa Xaa

```
<210> SEQ ID NO 26
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 26
```

Arg Phe Arg Gly Val Lys Lys Ile Leu Val Gly Xaa Xaa Xaa Xaa
              5                    10               15

Xaa Xaa Xaa Xaa Xaa Xaa Xaa Xaa
        20

```
<210> SEQ ID NO 27
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:
<221> NAME/KEY: MISC_FEATURE
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 27
```

Lys Phe Arg Gly Val Lys Lys Ile Leu Val Gly Xaa Xaa Xaa Xaa
              5                    10               15

Xaa Xaa Xaa Xaa

```
<210> SEQ ID NO 28
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
```

```
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 28

Lys Phe Arg Gly Val Lys Lys Ile Leu Val Gly Xaa Xaa Xaa Xaa
                5                   10                  15

Xaa Xaa Xaa Xaa Xaa Xaa Xaa Xaa
                20

<210> SEQ ID NO 29
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:
<221> NAME/KEY: MISC_FEATURE
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 29

Arg Trp Arg Ile Gly Arg Arg Ile Val Leu Ala Xaa Xaa Xaa Xaa
                5                   10                  15

Xaa Xaa Xaa Xaa

<210> SEQ ID NO 30
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 30

Arg Trp Arg Ile Gly Arg Arg Ile Val Leu Ala Xaa Xaa Xaa Xaa
                5                   10                  15
```

```
Xaa Xaa Xaa Xaa Xaa Xaa Xaa Xaa
            20

<210> SEQ ID NO 31
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:
<221> NAME/KEY: MISC_FEATURE
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 31

Arg Trp Arg Ile Gly Lys Lys Ile Val Leu Ala Xaa Xaa Xaa Xaa
              5                   10                  15

Xaa Xaa Xaa Xaa

<210> SEQ ID NO 32
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 32

Arg Trp Arg Ile Gly Lys Lys Ile Val Leu Ala Xaa Xaa Xaa Xaa
              5                   10                  15

Xaa Xaa Xaa Xaa Xaa Xaa Xaa Xaa
            20

<210> SEQ ID NO 33
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:
<221> NAME/KEY: MISC_FEATURE
```

```
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 33

Lys Trp Arg Ile Gly Lys Lys Ile Val Leu Ala Xaa Xaa Xaa Xaa
                 5                   10                  15

Xaa Xaa Xaa Xaa

<210> SEQ ID NO 34
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 34

Lys Trp Arg Ile Gly Lys Lys Ile Val Leu Ala Xaa Xaa Xaa Xaa
                 5                   10                  15

Xaa Xaa Xaa Xaa Xaa Xaa Xaa Xaa
                20

<210> SEQ ID NO 35
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:
<221> NAME/KEY: MISC_FEATURE
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 35

Lys Trp Lys Ile Gly Lys Lys Ile Val Leu Ala Xaa Xaa Xaa Xaa
                 5                   10                  15
```

Xaa Xaa Xaa Xaa

<210> SEQ ID NO 36
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 36

Lys Trp Lys Ile Gly Lys Lys Ile Val Leu Ala Xaa Xaa Xaa Xaa
                 5                  10                  15

Xaa Xaa Xaa Xaa Xaa Xaa Xaa Xaa
             20

<210> SEQ ID NO 37
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:
<221> NAME/KEY: MISC_FEATURE
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 37

Arg Trp Arg Leu Phe Arg Arg Ile Gly Ile Gly Xaa Xaa Xaa Xaa
                 5                  10                  15

Xaa Xaa Xaa Xaa

<210> SEQ ID NO 38
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)

```
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 38

Arg Trp Arg Leu Phe Arg Arg Ile Gly Ile Gly Xaa Xaa Xaa Xaa
                 5                  10                  15

Xaa Xaa Xaa Xaa Xaa Xaa Xaa Xaa
                20

<210> SEQ ID NO 39
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:
<221> NAME/KEY: MISC_FEATURE
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 39

Arg Trp Arg Leu Phe Lys Arg Ile Gly Ile Gly Xaa Xaa Xaa Xaa
                 5                  10                  15

Xaa Xaa Xaa Xaa

<210> SEQ ID NO 40
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 40

Arg Trp Arg Leu Phe Lys Arg Ile Gly Ile Gly Xaa Xaa Xaa Xaa
                 5                  10                  15

Xaa Xaa Xaa Xaa Xaa Xaa Xaa Xaa
```

<210> SEQ ID NO 41
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:
<221> NAME/KEY: MISC_FEATURE
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 41

Arg Trp Arg Leu Phe Lys Lys Ile Gly Ile Gly Xaa Xaa Xaa Xaa
                 5                  10                  15

Xaa Xaa Xaa Xaa

<210> SEQ ID NO 42
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 42

Arg Trp Arg Leu Phe Lys Lys Ile Gly Ile Gly Xaa Xaa Xaa Xaa
                 5                  10                  15

Xaa Xaa Xaa Xaa Xaa Xaa Xaa Xaa
                 20

<210> SEQ ID NO 43
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:
<221> NAME/KEY: MISC_FEATURE
<222> LOCATION: (13,17)

```
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 43

Arg Trp Lys Leu Phe Lys Lys Ile Gly Ile Gly Xaa Xaa Xaa Xaa
                 5                  10                  15

Xaa Xaa Xaa Xaa

<210> SEQ ID NO 44
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 44

Arg Trp Lys Leu Phe Lys Lys Ile Gly Ile Gly Xaa Xaa Xaa Xaa
                 5                  10                  15

Xaa Xaa Xaa Xaa Xaa Xaa Xaa Xaa
                20

<210> SEQ ID NO 45
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:
<221> NAME/KEY: MISC_FEATURE
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 45

Lys Trp Lys Leu Phe Lys Lys Ile Gly Ile Gly Xaa Xaa Xaa Xaa
                 5                  10                  15

Xaa Xaa Xaa Xaa
```

<210> SEQ ID NO 46
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 46

Lys Trp Lys Leu Phe Lys Lys Ile Gly Ile Gly Xaa Xaa Xaa Xaa
                 5                  10                  15

Xaa Xaa Xaa Xaa Xaa Xaa Xaa Xaa
            20

<210> SEQ ID NO 47
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:
<221> NAME/KEY: MISC_FEATURE
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 47

Arg Phe Arg Val Ile Arg Arg Ile Leu Val Gly Xaa Xaa Xaa Xaa
                 5                  10                  15

Xaa Xaa Xaa Xaa

<210> SEQ ID NO 48
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe

```
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 48

Arg Phe Arg Val Ile Arg Arg Ile Leu Val Gly Xaa Xaa Xaa Xaa
                 5                  10                  15

Xaa Xaa Xaa Xaa Xaa Xaa Xaa Xaa
                20

<210> SEQ ID NO 49
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:
<221> NAME/KEY: MISC_FEATURE
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 49

Arg Phe Arg Val Ile Arg Lys Ile Leu Val Gly Xaa Xaa Xaa Xaa
                 5                  10                  15

Xaa Xaa Xaa Xaa

<210> SEQ ID NO 50
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 50

Arg Phe Arg Val Ile Arg Lys Ile Leu Val Gly Xaa Xaa Xaa Xaa
                 5                  10                  15

Xaa Xaa Xaa Xaa Xaa Xaa Xaa Xaa
                20
```

<210> SEQ ID NO 51
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:
<221> NAME/KEY: MISC_FEATURE
<222> LOCATION: (13,17)
<223> OTHER INFORMATION: Xaa=Gly or Ala or Val or Leu or Ile or Phe
<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 51

Arg Phe Arg Val Ile Lys Lys Ile Leu Val Gly Xaa Xaa Xaa Xaa
                 5                  10                  15

Xaa Xaa Xaa Xaa

<210> SEQ ID NO 52
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 52

Arg Phe Arg Val Ile Lys Lys Ile Leu Val Gly Xaa Xaa Xaa Xaa
                 5                  10                  15

Xaa Xaa Xaa Xaa Xaa Xaa Xaa Xaa
                 20

<210> SEQ ID NO 53
<211> LENGTH: 19
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16)
<223> OTHER INFORMATION: Xaa=Lys or Arg
<220> FEATURE:
<221> NAME/KEY: MISC_FEATURE
<222> LOCATION: (13,17)
<223> OTHER INFORMATION: Xaa=Gly or Ala or Val or Leu or Ile or Phe

```
-continued

<220> FEATURE:
<221> NAME/KEY: MISC_FEATURE
<222> LOCATION: (14,18)
<223> OTHER INFORMATION: Xaa=Gly or Ala or Val or Leu or Ile or Phe
<220> FEATURE:
<221> NAME/KEY: MISC_FEATURE
<222> LOCATION: (15,19)
<223> OTHER INFORMATION: Xaa=Lys or Arg

<400> SEQUENCE: 53

Lys Phe Lys Val Ile Lys Lys Ile Leu Val Gly Xaa Xaa Xaa Xaa
                 5                   10                  15

Xaa Xaa Xaa Xaa

<210> SEQ ID NO 54
<211> LENGTH: 23
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (12,16,20)
<223> OTHER INFORMATION: Xaa=Lys or Arg
<220> FEATURE:
<221> NAME/KEY: MISC_FEATURE
<222> LOCATION: (13,17,21)
<223> OTHER INFORMATION: Xaa=Gly or Ala or Val or Leu or Ile or Phe
<220> FEATURE:
<221> NAME/KEY: MISC_FEATURE
<222> LOCATION: (14,18,22)
<223> OTHER INFORMATION: Xaa=Gly or Ala or Val or Leu or Ile or Phe
<220> FEATURE:
<221> NAME/KEY: MISC_FEATURE
<222> LOCATION: (15,19,23)
<223> OTHER INFORMATION: Xaa=Lys or Arg

<400> SEQUENCE: 54

Lys Phe Lys Val Ile Lys Lys Ile Leu Val Gly Xaa Xaa Xaa Xaa
                 5                   10                  15

Xaa Xaa Xaa Xaa Xaa Xaa Xaa Xaa
                 20
```

GROUP OF SYNTHETIC ANTIMICROBIAL PEPTIDES

This application is a national stage filing under 35 U.S.C. § 371 of PCT International application PCT/CN03/00522, filed Jul. 1, 2003, and claims priority under 35 U.S.C. §119(a) to China Patent Application number 02136766.6 filed Sep. 2, 2002.

FIELD OF THE INVENTION

This invention relates generally to antimicrobial peptides, the methods for preparing these peptides and methods for inhibiting the growth of microbes such as bacteria, yeast and viruses utilizing the peptides of the invention. The peptides are also useful for inhibiting tumor cell.

BACKGROUND OF THE INVENTION

The recent research data have revealed that, besides their immune systems, almost all living organisms have an additional defense system against invasion of pathogenic microorganisms. They produce antimicrobial peptides in their bodies and use them as a defense means against pathogenic microorganisms. Antimicrobial peptides are composed of 20-60 amino acids, and their molecular weights are about 2000-7000 D. Thus far, as many as about 200 antimicrobial peptides have been found from amphibians, insects, mammals, plants, microorganisms and fishes. The importance of peptides as physiologically active materials has been greatly recognized. These antimicrobial peptides are showing antimicrobial activity against a broad spectrum of microorganisms, including Gram-negative bacteria, Gram-positive bacteria, protozoa and fungi. Some of them are effective against both cancer cells and viruses. Most of the antimicrobial peptides kill target cells rapidly and specifically, and have unusually broad activity spectra.

By researching the primary structure and higher-order structure of the antimicrobial peptide, a lot of researcher find that when the antimicrobial peptide is in the hydrophobic environment of mimic membrane, its antimicrobial activity is related with the α-helix proportion. Another research result indicates that antimicrobial peptide kills the microorganisms by destructing the intact membrane of the microorganisms, which makes the membrane of the microorganisms leakage (Nakajima Y. et al., J. Biol. Chem, 262:1665-1669; Zasloff M. Nature, 2002, 415:389-395). So someone tries to search the antimicrobial peptides having stronger antimicrobial activity by increasing α-helix structure or heightening the positive charge amino acids proportion in the antimicrobial peptides (Broth W. B. et al., Antimicrobial Agents Chemotherapy, 2001, 45:1894-1895; Hong S. Y. et al., Peptides, 2001, 22:1669-1674).

DISCLOSURE OF THE INVENTION

The present invention provides a group of synthetic antimicrobial peptides. They were designed on the basis of analysis of the native antimicrobial peptides. The sequences of the peptides of the invention are provided as follows:

```
Arg Phe Arg Leu Val Arg Arg Ile Val Leu Ala (A1-A2-A3-A4)(A1'-A2'-A3'-A4')
(SEQ ID NO: 1)

Arg  Phe  Arg  Leu  Val  Arg  Arg  Ile  Val  Leu  Ala
(A1-A2-A3-A4)(A1'-A2'-A3'-A4')(A1"-A2"-A3"-A4")
(SEQ ID NO: 2)

Arg Phe Lys Leu Val Arg Arg Ile Val Leu Ala (A1-A2-A3-A4)(A1'-A2'-A3'-A4')
(SEQ ID NO: 3)

Arg  Phe  Lys  Leu  Val  Arg  Arg  Ile  Val  Leu  Ala
(A1-A2-A3-A4)(A1'-A2'-A3'-A4')(A1"-A2"-A3"-A4")
(SEQ ID NO: 4)

Arg Phe Lys Leu Val Lys Arg Ile Val Leu Ala (A1-A2-A3-A4)(A1'-A2'-A3'-A4')
(SEQ ID NO: 5)

Arg  Phe  Lys  Leu  Val  Lys  Arg  Ile  Val  Leu  Ala
(A1-A2-A3-A4)(A1'-A2'-A3'-A4')(A1"-A2"-A3"-A4")
(SEQ ID NO: 6)

Arg Phe Lys Leu Val Lys Lys Ile Val Leu Ala (A1-A2-A3-A4)(A1'-A2'-A3'-A4')
(SEQ ID NO: 7)

Arg  Phe  Lys  Leu  Val  Lys  Lys  Ile  Val  Leu  Ala
(A1-A2-A3-A4)(A1'-A2'-A3'-A4')(A1"-A2"-A3"-A4")
(SEQ ID NO: 8)

Lys Phe Lys Leu Val Lys Lys Ile Val Leu Ala (A1-A2-A3-A4)(A1'-A2'-A3'-A4')
(SEQ ID NO: 9)

Lys  Phe  Lys  Leu  Val  Lys  Lys  Ile  Val  Leu  Ala
(A1-A2-A3-A4)(A1'-A2'-A3'-A4')(A1"-A2"-A3"-A4")
(SEQ ID NO: 10)

Arg Phe Arg Leu Phe Arg Arg Ile Leu Val Gly (A1-A2-A3-A4)(A1'-A2'-A3'-A4')
(SEQ ID NO: 11)

Arg  Phe  Arg  Leu  Phe  Arg  Arg  Ile  Leu  Val  Gly
(A1-A2-A3-A4)(A1'-A2'-A3'-A4')(A1"-A2"-A3"-A4")
(SEQ ID NO: 12)
```

-continued

Arg Phe Lys Leu Phe Arg Arg Ile Leu Val Gly (A1-A2-A3-A4)(A1'-A2'-A3'-A4')
(SEQ ID NO: 13)

Arg Phe Lys Leu Phe Arg Arg Ile Leu Val Gly
(A1-A2-A3-A4)(A1'-A2'-A3'-A4')(A1"-A2"-A3"-A4")
(SEQ ID NO: 14)

Arg Phe Lys Leu Phe Lys Arg Ile Leu Val Gly (A1-A2-A3-A4)(A1'-A2'-A3'-A4')
(SEQ ID NO: 15)

Arg Phe Lys Leu Phe Lys Arg Ile Leu Val Gly
(A1-A2-A3-A4)(A1'-A2'-A3'-A4')(A1"-A2"-A3"-A4")
(SEQ ID NO: 16)

Arg Phe Lys Leu Phe Lys Lys Ile Leu Val Gly (A1-A2-A3-A4)(A1'-A2'-A3'-A4')
(SEQ ID NO: 17)

Arg Phe Lys Leu Phe Lys Lys Ile Leu Val Gly
(A1-A2-A3-A4)(A1'-A2'-A3'-A4')(A1"-A2"-A3"-A4")
(SEQ ID NO: 18)

Lys Phe Lys Leu Phe Lys Lys Ile Leu Val Gly (A1-A2-A3-A4)(A1'-A2'-A3'-A4')
(SEQ ID NO: 19)

Lys Phe Lys Leu Phe Lys Lys Ile Leu Val Gly
(A1-A2-A3-A4)(A1'-A2'-A3'-A4')(A1"-A2"-A3"-A4")
(SEQ ID NO: 20)

Arg Phe Arg Gly Val Arg Arg Ile Leu Val Gly (A1-A2-A3-A4)(A1'-A2'-A3'-A4')
(SEQ ID NO: 21)

Arg Phe Arg Gly Val Arg Arg Ile Leu Val Gly
(A1-A2-A3-A4)(A1'-A2'-A3'-A4')(A1"-A2"-A3"-A4")
(SEQ ID NO: 22)

Arg Phe Arg Gly Val Lys Arg Ile Leu Val Gly (A1-A2-A3-A4)(A1'-A2'-A3'-A4')
(SEQ ID NO: 23)

Arg Phe Arg Gly Val Lys Arg Ile Leu Val Gly
(A1-A2-A3-A4)(A1'-A2'-A3'-A4')(A1"-A2"-A3"-A4")
(SEQ ID NO: 24)

Arg Phe Arg Gly Val Lys Lys Ile Leu Val Gly (A1-A2-A3-A4)(A1'-A2'-A3'-A4')
(SEQ ID NO: 25)

Arg Phe Arg Gly Val Lys Lys Ile Leu Val Gly
(A1-A2-A3-A4)(A1'-A2'-A3'-A4')(A1"-A2"-A3"-A4")
(SEQ ID NO: 26)

Lys Phe Arg Gly Val Lys Lys Ile Leu Val Gly (A1-A2-A3-A4)(A1'-A2'-A3'-A4')
(SEQ ID NO: 27)

Lye Phe Arg Gly Val Lys Lys Ile Leu Val Gly
(A1-A2-A3-A4)(A1'-A2'-A3'-A4')(A1"-A2"-A3"-A4")
(SEQ ID NO: 28)

Arg Trp Arg Ile Gly Arg Arg Ile Val Leu Ala (A1-A2-A3-A4)(A1'-A2'-A3'-A4')
(SEQ ID NO: 29)

Arg Trp Arg Ile Gly Arg Arg Ile Val Leu Ala
(A1-A2-A3-A4)(A1'-A2'-A3'-A4')(A1"-A2"-A3"-A4")
(SEQ ID NO: 30)

Arg Trp Arg Ile Gly Lys Lys Ile Val Leu Ala (A1-A2-A3-A4)(A1'-A2'-A3'-A4')
(SEQ ID NO: 31)

Arg Trp Arg Ile Gly Lys Lys Ile Val Leu Ala
(A1-A2-A3-A4)(A1'-A2'-A3'-A4')(A1"-A2"A3"-A4")
(SEQ ID NO: 32)

Lys Trp Arg Ile Gly Lys Lys Ile Val Leu Ala (A1-A2-A3-A4)(A1'-A2'-A3'-A4')
(SEQ ID NO: 33)

Lys Trp Arg Ile Gly Lys Lys Ile Val Leu Ala
(A1-A2-A3-A4)(A1'-A2'-A3'-A4')(A1"-A2"-A3"-A4")
(SEQ ID NO: 34)

Lys Trp Lys Ile Gly Lys Lys Ile Val Leu Ala (A1-A2-A3-A4)(A1'-A2'-A3'-A4')
(SEQ ID NO: 35)

-continued

```
Lys Trp Lys Ile Gly Lys Lys Ile Val Leu Ala
(A1-A2-A3-A4)(A1'-A2'-A3'-A4')(A1"-A2"-A3"-A4")
(SEQ ID NO: 36)

Arg Trp Arg Leu Phe Arg Arg Ile Gly Ile Gly (A1-A2-A3-A4)(A1'-A2'-A3'-A4')
(SEQ ID NO 37)

Arg Trp Arg Leu Phe Arg Arg Ile Gly Ile Gly
(A1-A2-A3-A4)(A1'-A2'-A3'-A4')(A1"-A2"-A3"-A4")
(SEQ ID NO: 38)

Arg Trp Arg Leu Phe Lys Arg Ile Gly Ile Gly (A1-A2-A3-A4)(A1'-A2'-A3'-A4')
(SEQ ID NO: 39)

Arg Trp Arg Leu Phe Lys Arg Ile Gly Ile Gly
(A1-A2-A3-A4)(A1'-A2'-A3'-A4')(A1"-A2"-A3"-A4")
(SEQ ID NO: 40)

Arg Trp Arg Leu Phe Lys Lys Ile Gly Ile Gly (A1-A2-A3-A4)(A1'-A2'-A3'-A4')
(SEQ ID NO: 41)

Arg Trp Arg Leu Phe Lys Lys Ile Gly Ile Gly
(A1-A2-A3-A4)(A1'-A2'-A3'-A4')(A1"-A2"-A3"-A4")
(SEQ ID NO: 42)

Arg Trp Lys Leu Phe Lys Lys Ile Gly Ile Gly (A1-A2-A3-A4)(A1'-A2'-A3'-A4')
(SEQ ID NO: 43)

Arg Trp Lys Leu Phe Lys Lys Ile Gly Ile Gly
(A1-A2-A3-A4)(A1'-A2'-A3'-A4')(A1"-A2"-A3"-A4")
(SEQ ID NO: 44)

Lys Trp Lys Leu Phe Lys Lys Ile Gly Ile Gly (A1-A2-A3-A4)(A1'-A2'-A3'-A4')
(SEQ ID NO: 45)

Lys Trp Lys Leu Phe Lys Lys Ile Gly Ile Gly
(A1-A2-A3-A4)(A1'-A2'-A3'-A4')(A1"-A2"-A3"-A4")
(SEQ ID NO: 46)

Arg Phe Arg Val Ile Arg Arg Ile Leu Val Gly (A1-A2-A3-A4)(A1'-A2'-A3'-A4')
(SEQ ID NO: 47)

Arg Phe Arg Val Ile Arg Arg Ile Leu Val Gly
(A1-A2-A3-A4)(A1'-A2'-A3'-A4')(A1"-A2"-A3"-A4")
(SEQ ID NO: 48)

Arg Phe Arg Val Ile Arg Lys Ile Leu Val Gly (A1-A2-A3-A4)(A1'-A2'-A3'-A4')
(SEQ ID NO: 49)

Arg Phe Arg Val Ile Arg Lys Ile Leu Val Gly
(A1-A2-A3-A4)(A1'-A2'-A3'-A4')(A1"-A2"-A3"-A4")
(SEQ ID NO: 50)

Arg Phe Arg Val Ile Lys Lys Ile Leu Val Gly (A1-A2-A3-A4)(A1'-A2'-A3'-A4')
(SEQ ID NO: 51)

Arg Phe Arg Val Ile Lys Lys Ile Leu Val Gly
(A1-A2-A3-A4)(A1'-A2'-A3'-A4')(A1"-A2"-A3"-A4")
(SEQ ID NO: 52)

Lys Phe Lys Val Ile Lys Lys Ile Leu Val Gly (A1-A2-A3-A4)(A1'-A2'-A3'-A4')
(SEQ ID NO: 53)

Lys Phe Lys Val Ile Lys Lys Ile Leu Val Gly
(A1-A2-A3-A4)(A1'-A2'-A3'-A4')(A1"-A2"-A3"-A4")
(SEQ ID NO: 54)
```

(A1-A2-A3-A4)(A1'-A2'-A3'-A4') or (A1-A2-A3-A4)(A1'-A2'-A3'-A4')(A1"-A2"-A3"-A4") is the core structure of the antimicrobial peptides. A1, A1' or A1" is one selected from the group consisting of Lys and Arg. A2, A2' or A2" is one selected from the group consisting of Gly, Ala, Val, Leu, Ile and Phe. A3, A3' or A3" is one selected from the group consisting of Gly, Ala, Val, Leu, Ile and Phe. A4, A4' or A4" is one selected from the group consisting of Lys and Arg. The N-terminal end of the core structure (A1-A2-A3-A4) is linked with a sequence having 11 amino acids. The first or third or sixth or seventh amino acid of the sequence is one selected from the group consisting of Lys and Arg. The second amino acid of the sequence is one selected from the group consisting of Trp and Phe. The fourth or fifth or eighth or ninth or tenth or eleventh amino acid of the sequence is one selected from the group consisting of Leu, Ile, Ala, Val and Gly.

The synthetic peptides provided by the invention comprise their functional analogs derived from amino acid substitution, cyclization, replacement of L-amino acid with D-amino acid, deletion or addition.

One method for producing the peptides provided by the invention is solid-phase peptide synthesis. The other method for producing the peptide is expressing a nucleic acid sequence encoding the peptide in a host cell transformed with a recombinant vector. Then the peptide is expressed in the host cell. The vector is one selected from the group consisting of plasmid and virus. The host cell can be a prokaryotic cell, including *Escherichia coli* and *Bacillus subtilis*. The host cell also can be a eukaryotic cell, including yeast cell, plant cell, insect cell and mammal cell. The peptide can be detected by mass-spectroscopy.

In order to research the relation between the structure and the function of the antimicrobial peptides provided by the invention, we used peptide synthesizer, which was purchased from ABI, to produce a group of peptides. Presented below are examples of the solid phase synthesis of these peptides. The sequences of GK-1, GK-2, GK-3 are provided as below.

```
GK-1:
Lys Trp Lys Leu Phe Lys Lys Ile Gly Ile Gly Arg

Leu Leu Lys Arg Gly Leu Arg Lys Leu Leu Lys (SEQ ID NO: 55)

GK-2:
Lys Trp Lys Leu Phe Lys Lys Ile Gly Ile Gly Arg

Leu Leu Arg Arg Leu Leu Arg Arg Leu Leu Arg (SEQ ID NO: 56)

GK-3:
Arg Trp Arg Leu Phe Lys Arg Ile Gly Ile Gly Arg

Leu Leu Lys Arg Gly Leu Arg (SEQ ID NO: 57)
```

To assay the MIC of three peptides GK-1, GK-2 and GK-3 of the present invention, 96-well microtiter plate was used (In Yup Park et al; FEBS Letters; 437 (1998) 258-262), cecropin A1 and buforin II as control. The result indicated that the bactericidal activity of the peptides provided by the invention were stronger than the two native antimicrobial peptides.

Synthesis and detection the MIC of the functional analogs of the peptides were provided by the invention, which were deletion derivative and cyclization derivative. The result indicated that the bactericidal activity of the peptides provided by the invention were stronger than the two native antimicrobial peptides.

When the antimicrobial peptides kill the bacteria, they may act on the higher organism, include human cells. The reason is that the antimicrobial peptide kills the microorganisms by destructing the intact membrane of the microorganisms, which makes the leakage of the membrane of the microorganisms. So the hemolytic activity of the antimicrobial peptides is one of the standards of the toxicity of the antimicrobial peptides. If the peptides make the hematoglobin release, then the number of the $OD_{490}$ can confirm the intensity of the toxicity of the antimicrobial peptides. This experiment in the invention detected the hemolytic activity on the human red blood cells of the antimicrobial peptides. The results indicated that the hemolytic rate was very small, to confirm that the hemolytic activity of antimicrobial peptide was very low.

The results of acute toxicity test in Kunming mouse of the antimicrobial peptides indicated that the peptides had no toxicity. The experiment of the efficacy of antimicrobial peptide against the *Staphylococcus aureus* infection in mice demonstrated that antimicrobial peptide provided by the invention was effective against *S. aureus* infection in an acute infection model in mice.

The invention provides a group of new synthetic antimicrobial peptides. They can be produced by the method of solid-phase peptide synthesis. The other method for producing the peptide is expressing a nucleic acid sequence encoding the peptide in a host cell transformed with a recombinant vector. Then the peptide is expressed in the host cell. The antimicrobial peptides have broad spectral bactericidal activity on Gram-positive bacteria, Gram-negative bacteria, fungi. The bactericidal activity of the peptides are stronger than the native antimicrobial peptides. The peptides have no toxicity to animal and plant cells. The peptides protected completely from the *Staphylococcus aureus* infection in mice when administered at a dosage of 0.25 mg/kg, while Vancomycin, which was a specific medicine for *Staphylococcus aureus*, was 100% effective only at the dosage of 4.5 mg/kg. The results demonstrated that antimicrobial peptide provided by the invention was effective against *S. aureus* infection in an acute infection model in mice. The antimicrobial peptides provided by the invention can be used to produce the drug to treat the diseases induced by Gram-positive bacteria, Gram-negative bacteria, and fungi.

The peptides of the present can be used to prepare a drug for treating the pathologic microbes, fungus and/or virus infectious diseases.

The peptides of the present invention can also be used to prepare an antitumor drug.

EXAMPLES

Example 1

Preparation and Purification of Antimicrobial Peptide

Figure 1:
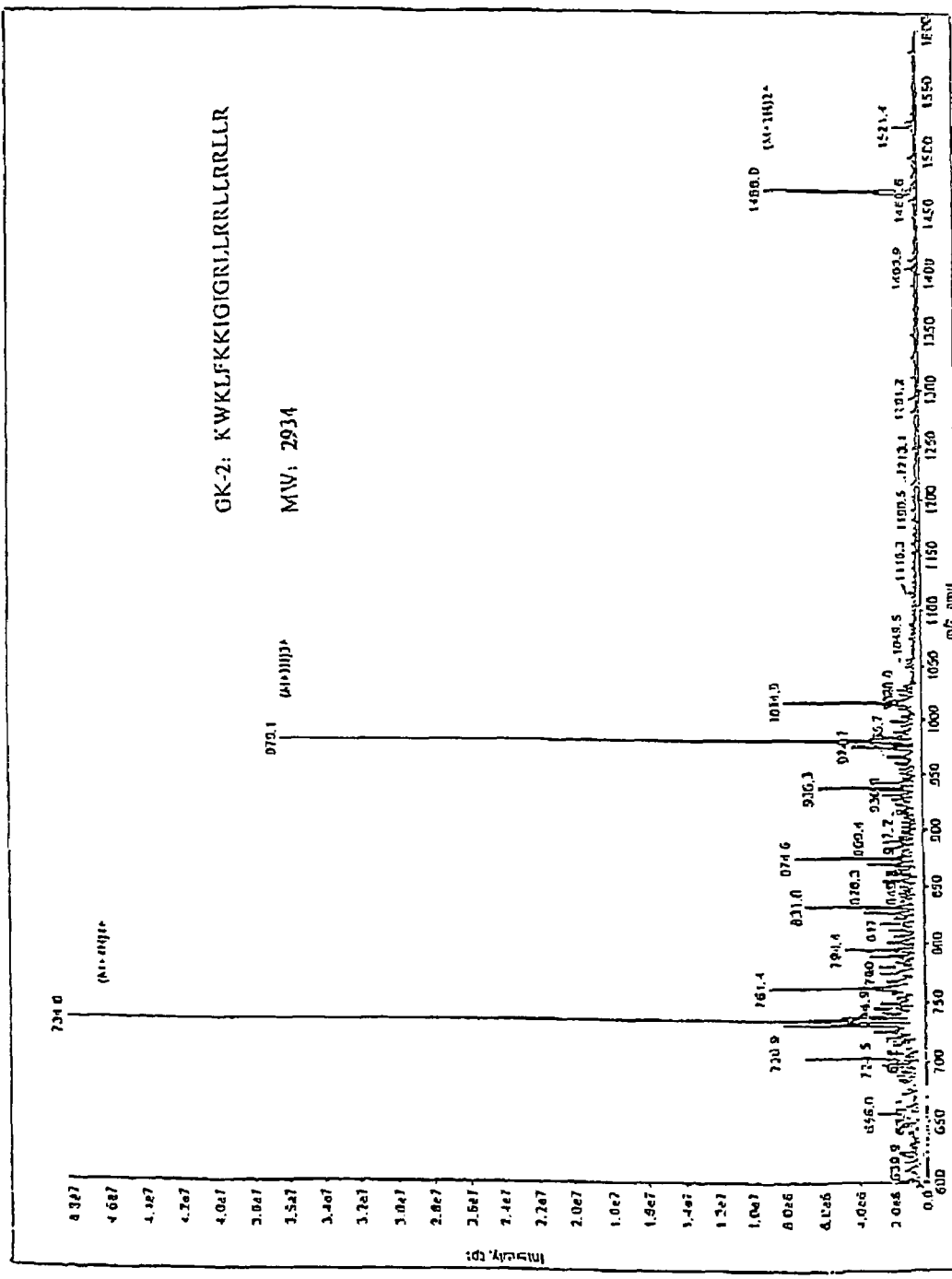
FIG. 1 is mass-spectrogram for the antimicrobial peptide GK-2.

Prepare GK-1, GK-2 and GK-3. Prepare cecropin A1 and buforin II as control.

Sequence of cecropin A1 (see Morishima, I., etc, Comp. Biochem. Physiol., 1990, B 95 (3), 551-554):

```
Arg Trp Lys Leu Phe Lys Lys Ile Glu Lys Val Gly

Arg Asn Val Arg Asp Gly Leu Ile Lys Ala Gly Pro

Ala Ile Ala Val Ile Gly Gln Ala Lys Ser Leu (SEQ ID NO: 58)
```

Sequence of buforin II (see Park, C. B., Biochem. Biophys. Res. Commun. 1996, 218 (1), 408-413):

```
Thr Arg Ser Ser Arg Ala Gly Leu Gln Phe Pro

Val Gly Arg Val His Arg Leu Leu Arg Lys (SEQ ID NO: 59)
```

Presented below are examples of the solid phase synthesis of these peptides. The peptide synthesizer was purchased from ABI, USA. After cleaving with high concentration TFA, the peptide was purified by reverse-phase column. The purified peptide was then analyzed by MS. The procedures in detail are provided as follows:

1. Preparation of antimicrobial peptide (GK-2, 0.1 mmol)

All reagents are purchased from ABI, USA.

The sequence of peptide GK-2 is

N-Lys Trp Lys Leu Phe Lys Lys Ile Gly Ile Gly Arg

Leu Leu Arg Arg Leu Leu Arg Arg Leu Leu Arg-C.

(SEQ ID NO: 56)

The Pioneer Peptide Synthesis System performs solid-phase synthesis, in which peptide chains are assembled on a solid support from the C-terminus, one amino acid at a time, elongating the chain toward the N-terminus. Calculate the amount of support (Fmoc-Arg(Pbf)-PEG-PS, purchased from ABI, loading factor 0.19 mmole/g) needed for the synthesis. Weigh the support and transfer it to the column. Removal of the Fmoc (9-fluorenyl-methyloxycarbonyl) protecting group from the terminal amine or the resin is accomplished by treating the resin with 20% solution of piperidine in N,N-Dimethylformamide (DMF). The required volume of the 20% solution of piperidine in DMF is calculated automatically on the scale of the reaction being run. The resin is then washed with DMF. The 9-fluorenyl-methyloxycarbonyl (Fmoc) protected amino acid was dissolved in O-(7-Azabenzotriazol-1-yl)-N,N,N',N'-tetramethyluronium exafluorophosphate (HATU)/diisopropylethylamine (DIPEA). The solution was recycled through the column for 30 minutes. The resin is then washed with DMF. Repeat the steps from removal to coupling till the end of synthesis (see *Pioneer Peptide Synthesiser User's manual* for details).

The resulting peptides were cleaved as follows:

After reaction, the resin was removed, to which was added B type cleavage cocktail (88% TFA, 5% phenol, 5% water, 2% TIPS), continue to reaction for about 2 hours at room temperature. Filtering, and to the filtrate was added 10-fold volume of pre-cold absolute ether. The precipitate was collected by centrifugation at 4000 rpm for 10 minutes, and dried at room temperature.

2. Purification of antimicrobial peptide

Weigh an amount of dried peptide, resolved in 0.1% TFA. The peptide was purified by reverse-phase column (elution: 80% acetonitrile/0.1% TFA). Collect the elution fraction.

3. Identification of antimicrobial peptide

As shown in FIG. 1, the molecular weight of antimicrobial peptide GK-2 is analyzed and calculated by MS:

$$734.8 \times 4 = 2939.2, 2939.2 - 4 = 2935.2 \quad (1)$$

$$979.1 \times 3 = 2937.3, 2937.3 - 3 = 2934.3 \quad (2)$$

$$1468 \times 2 = 2936, 2936 - 2 = 2934 \quad (3)$$

The calculated MW of GK-2 is 2934. The theory value calculated from the peptide sequence is 2932.74. The peptide prepared proved to be the designed GK-2 antimicrobial peptide. The certified antimicrobial peptide is stored for further use.

Antimicrobial peptide GK-1, GK-3 and natural antimicrobial peptides cecropin A1 and buforin II were prepared similarly to the preparation of GK-2 antimicrobial peptide.

Example 2

Expression of Antimicrobial Peptide GK-1 Gene in *E. coli*

The bacterial expression vector pGEX-4T1 is used for bacterial expression in this example (Amersham Pharmcia Biotech). Antimicrobial peptide gene GK-1 was designed and synthesized and cloned into pGEX-4T1, then the expression vector containing GK-1 was transformed into *E. coli* JM109, GST-GK-1 fusion protein was expressed by IPTG inducing, GK-1 was obtained after cleaving by thrombin.

ATP, IPTG, T4 polynucleotide kinase, $T_4$DNA ligase, Klenow Fragment, Restriction endonucleases are products of BIOLAB except for special indication. The agarose gel DNA extraction kit is product of shanghai sangon, primers for PCR amplification were synthesized by shanghai sangon. Thrombin cleavage kit from sigma.

With respect to the methods of DNA separation, purification, PCR reaction enzyme cleavage, plasmid transformation, fragment collection, link reaction etc. are referred to Molecular Cloning: A Laboratory Manual (edited by Joe Sambrook, David Russell, Cold Spring Harbor Lab (CSHL) Press, 2001). *E. coli* JM109 was cultured in LB liquid or solid medium.

We use *E. coli* bias coden design GK-1 gene sequence, the sequence as following: For cloning the mature protein, the 5' primer containing the BamHI (GGATCC) restriction site, The 3' primer containing the stop coden (TAG), the sequence contain 78 bp.

The sequence of GK-1 gene was synthesized by DNA synthesizer. A DNA segment was amplified by PCR reaction. A pair of primers were P1: 5'-CCTAGGTTTACCT-3'和(SEQ ID NO: 60) P2: 3'-CCGCCTGCTGAA-5'(SEQ ID NO: 61). PCR reaction was as following: 94° C. 30 seconds; 45° C., 45 seconds; 72° C., 30 seconds; 30 cycles. The PCR product was cleaved by BamHI after it reacted with Klenow fragment. The fragment collected by agarose gel DNA extraction kit (procedure see the kit). The recycled fragment linked with pGEX-4T1 vector which was cleaved by BamHI and SmaI, the recombinant plasmid transformed *E. coli* JM109, then transformants identified by SmaI. The fusion protein GST-GK-1 was induced to be expressed by IPTG. The fusion protein was purified by GST affinity column, and GK-1 antimicrobial peptide was obtained after it cleaved by thrombin. For the procedure, please see the kit.

GK-1 polypeptide sequence:

Lys Trp Lys Leu Phe Lys Lys Ile Gly Ile Gly Arg

Leu Leu Lys Arg Gly Leu Arg Lys Leu Leu Lys (SEQ ID NO: 55)

GK-1 gene sequence:

GGATCCAAATGGAAACTGTTTAAAAAAATTGGCATTGGCCGCCTGCTGA

ACGCGGCCTGCGCAAGCTGCTGAAATAG (SEQ ID NO: 62)

Example 3

Expression of Antimicrobial Peptide GK-1 Gene in Yeast

ATP, IPTG, T4 polynucleotide kinase, T₄DNA ligase, Klenow Fragment, Restriction Endonucleases are products of BIOLAB except for special indication. The agarose gel DNA extraction kit is product of shanghai sangon, primers for PCR amplification were synthesized by shanghai sangon. Thrombin cleavage kit is available from sigma.

The DNA sequence of GK-1 gene which was cleaved by BamHI linked with the DNA sequence of GST, then the linked gene was cloned into pBluescriptSKII (from Stratagene company, USA). Recombinant plasmid was transformed into *E. coli* DH5α (from CMCC, Wuhan, P.R.C). The plasmid was identified by DNA sequencing. The plasmid was cleaved by EcoRI and XhoI, then linked to yeast expression vector pPIC9. pPIC9 is used for yeast expression in this example (from invitrogen). The expression vector containing GK-1 was then transformed into KM71 (from Invitrogen company, USA), GST-GK-1 fusion protein was induced to be expressed by methyl alcohol, and GK-1 was obtained after cleavage by thrombin.

With respect to the methods of DNA separation, purification, PCR reaction, enzyme cleavage, plasmid transformation, fragment collection, ligase reaction etc. are referred to Molecular Cloning: A Laboratory Manual (edited by Joe Sambrook, David Russell, Cold Spring Harbor Lab (CSHL) Press, 2001). KM71 was cultured in BMGY liquid or solid medium. When GST-GK-1 fusion protein was expressed, BMMY medium was used. BMMY medium supplied methyl alcohol to 1% every 24 hours.

We use yeast bias coden design GK-1 and GST gene sequence, the sequence as follows: For cloning the mature protein, the 5' primer containing the BamHI (GGATCC) restriction site, The 3' primer containing the stop coden (TAG) and EcoRI (GAATCC) restriction site, the sequence contain 84 bp. Additional a XhoI (CTCGAG) restriction site at 5'-terminal of the GST was supplied.

Preparation of the sequence of GK-1 gene: the sequence of GK-1 gene was synthesized by DNA synthesizer. Amplify a DNA segment by PCR reaction. A pair of primer were P3: 5'CCTAGGTTTACCT3' (SEQ ID NO: 60) and P4: 5'AAGTCGTCCGCC 3' (SEQ ID NO: 61). PCR reaction is performed as follows: 94° C., 30 seconds; 45° C., 45 seconds; 72° C., 30 seconds; 35 cycles.

Preparation of the sequence of GST gene: designed a pair of primers, the sequences were as follows:

```
5'-CTCGAGATGTCCCTATACTAGGTT-3';  (SEQ ID NO: 63)

5'-CAGTGCTACGCCGGCGAG-3'.        (SEQ ID NO: 64)
```

Amplify the GST gene segment of pGEX-4T1 vector by PCR reaction with P5 and P6. PCR reaction is performed as follows: 94° C., 30 seconds; 45° C., 45 seconds; 72° C., 30 seconds; 30 cycles.

Link the PCR products to plasmid: GK-1 PCR products is cleaved by BamHI/EcoRI after reacting with Klenow fragment. The fragment was collected by agarose gel DNA extraction kit (see the kit manual for details). The recycled fragment was linked with pBluescriptSKII vector which was cleaved by XhoI/EcoRI and GST PCR products which were cleaved by BamHI/XhoI. *E. coli* DH5α was transformed by the recombinant plasmid. The transformants were identified by antibiotic resistance test, restriction endonucleases etc, and then was identified further by DNA sequencing and cleaved by XhoI/EcoRI. The expression plasmid pPIC9-gst-gk1 was constructed by linking the plasmid to pPIC9 vector which was cleaved by XhoI/EcoRI. The recombinant plasmid transformed *E. coli* DH5α. Scan transformants by Ampicillin resistance test. Prepare the KM71 competent cell (Clare J J, et al., Gene, 1991, 105:205-212). Then transported (1.5 KV, 22.5 uF) the recombinant plasmid pPIC9-gst-gk1 cleaved with SacI into KM71 cell. Spreaded the electroporated yeast onto YPD plate, scanned for the fusion protein positive clone after being cultured two days at 30° C.

The fusion protein GST-GK-1 was induced to be expressed by methanol in transformant. The fusion protein was purified by GST affinity column and obtained GK-1 antimicrobial peptide after cleavage with thrombin. See the kit manual for details.

GST-GK-1 fusion protein sequence:

Leu Glu Met Ser Pro Ile Leu Gly Tyr Trp Lys Ile Lys Gly Leu Val Gln Pro Thr Arg Leu Leu Leu Glu Tyr Leu Glu Glu Lys Tyr Glu Glu His Leu Tyr Glu Arg Asp Glu Gly Asp Lys Trp Arg Asn Lys Lys Phe Glu Leu Gly Leu Glu Phe Pro Asn Leu Pro Tyr Tyr Ile Asp Gly Asp Val Lys Leu The Gln Ser Met Ala Ile Ile Arg Tyr Ile Ala Asp Lys His Asn Met Leu Gly Gly Cys Pro Lys Glu Arg Ala Glu Ile Ser Met Leu Glu Gly Ala Val Leu Asp Ile Arg Tyr Gly Val Ser Arg Ile Ala Tyr Ser Lys Asp Phe Glu The Leu Lys Val Asp Phe Leu Ser Lys Leu Pro Glu Met Leu Lys Met Phe Glu Asp Arg Leu Cys His Lys The Tyr Leu Asn Gly Asp His Val The His Pro Asp Phe Met Leu Tyr Asp Ala Leu Asp Val Val Leu Tyr Met Asp Pro Met Cys Leu Asp Ala Phe Pro Lys Leu Val Cys Phe Lys Lys Arg (SEQ ID NO: 65)

Ile Glu Ala Ile Pro Gln Ile Asp Lys Tyr Leu Lys Ser Ser Lys Tyr Ile Ala Trp Pro Leu Gln Gly Trp Gln Ala The Phe Gly Gly Gly Asp His Pro Pro Lys Ser Asp Leu Val Pro Arg Gly Ser Lys Trp Lys Leu Phe Lys Lys Ile Gly Ile Gly Arg Leu Leu Lys Arg Gly Leu Arg Lys Leu Leu Lys (SEQ ID NO: 66)

GST-GK-1 gene sequence:

TTAGAAATGTCTCCTATTTTAGGTTAT-TGGAAAATTAAAGGTTTAGTTCAACC TACTCGTT-TATTATTAGAATATTTAGAA-GAAAAATATGAAGAACATTTATATGA ACGTGATGAAGGTGATAAATGGCG-TAATAAAAAATTTGAATTAGGTTTAGAAT TTC-CTAAATTTACCTTATTATATTGATGGT-GATGTTAAATTAACTCAATCTATGG CTATTATTCGTTATATTGCTGATAAA-CATAATATGTTAGGTGGTTGTCCTAAA GAACGTGCT-GAAATTTCTATGTTAGAAGGTGCTGTTT-TAGATATTCGTTATGG TGTTTCTCGTATTGCTTATTCTAAA-GATTTTGAAACTTTAAAAGTTGATTTTTT ATCTAAATTACCTGAAATGTTAAAAAT-GTTTGAAGATCGTTTATGTCATAAAAC TTATT-TAAATGGTGATCATGTTACTCATCCT-GATTTTATGTTATATGATGCTTT AGATGTTGTTTTATATATGGATCCTAT-GTGTTTAGATGCTTTTCCTAAATTAGT TTGTTT-TAAAAAACGTATTGAAGCTATTCCT-CAAATTGATAAATATTTAAAATC TTCTAAATATATTGCTTGGCCTTTA-CAAGGTTGGCAAGCTACTTTTGGTGGTG GTGAT-CATCCTCCTAAATCTGATTTAGTTC-CTCGTGGTTCTAAATGGAAATTA TTTAAAAAAATTGGTATTGGTCGTTTAT-TAAAACGTGGTTTACGTAAATTATTA AAAT-GAGAATTT (SEQ ID NO: 67)

Example 4

MIC Assay of Several Invention Peptides

All strains used in the following examples were purchased from NICPBP.

To assay the MIC of three peptides GK-1, GK-2 and GK-3 of the present invention, 96-well microtiter plate was used, cecropin A1 and buforin II as control.

The minimum inhibitory concentrations (MIC) of the invention peptides were determined using methods described below:

The strain was recovered, inoculated into sloped medium, and grown overnight at 37° C. Typical clone selected were grown overnight at 37° C. in LB culture, diluted in the same medium to give concentrations of about $10^4$-$10^5$ CFU/ml. The broth dilutions were set up in a 96-well microtiter plate by putting 100 μl of LB-S in every well. Added diluted peptide to every well (10 ul per well), cultured overnight at 37° C. The next day, the plates were scored for growth in the wells, and the MIC determined (In Yup Park et al.; FEBS Letters; 437 (1998) 258-262). Results were summarized in table 1.

When the ratio of the growth concentration for the bacteria with antimicrobial peptides to that for the bacteria without antimicrobial peptides is greater than 90%, the concentration of antimicrobial peptides is the minimum inhibitory concentration (The minimum inhibitory concentration (MIC) is defined as the minimal concentration when the growth of bacteria is significantly inhibited).

TABLE 1

Compare of MIC against different bacteria of five antimicrobial peptides

|  | Strain | \multicolumn{5}{c}{MIC of some antimicrobial peptides (ug/ml)} |
|---|---|---|---|---|---|---|
|  | Strain | cecropin A1 | buforin | <-1 | GK-2 | <-3 |
| G+ | Staphylococcus aureus CMCC26003 | 16 | 4 | 0.4 | 0.2 | 0.5 |
|  | Bacillus subtilis DB430 | 12 | 6 | 4 | 4 | 5 |
|  | Bacillus pumilus CMCC63202 | 50 | 6 | 0.5 | 1 | 0.8 |
|  | Micrococcus lysoleikticus S1.634 | 50 | 8 | 1.0 | 0.8 | 1.2 |
|  | Micrococcus lutea CMCC28001 | 30 | 8 | 2 | 4 | 3 |
| G- | Escherichia coli ATCC8099 | 20 | 16 | 1 | 0.5 | 1.6 |
|  | Klebsiella pneumoniae CMCC46117 | 16 | 20 | 2 | 0.8 | 2 |
|  | B Subacute sclerosing panencephalitis CMCC50094 | 12 | 14 | 4 | 1 | 6 |
|  | Pseudomonas aeruginosa CMCC10104 | 18 | 20 | 10 | 12 | 1.8 |
| Fungi | Candida albicans ATCC10231 | 50 | 30 | 8 | 10 | 11 |
|  | Saccharomyces cerevisiae ATCC9736 | 50 | 20 | 14 | 12 | 12 |

Lower MIC value means higher antimicrobial activity.

Example 5

MIC of Functional Analogs of Invention Peptides Derived from Cyclization, Deletion Design and synthesis functional analogs of invention peptides: GK-19 (deletion derivative) and GK-20 (cyclization derivative). Synthesis is performed on Pioneer Peptide Synthesiser. See *Pioneer Peptide Synthesiser User's manual* for details. After purification by reverse-phase column (see Example 1), the analogs were then subjected to MIC test (see Example 4). Results were summarized in Table 2. Sequences of GK-19 (deletion derivative) and GK-20 (cyclization derivative):

GK-19:

Arg Phe Lys Leu Phe Lys Lys Ile Pro Arg Leu Leu Arg Arg Gly Leu Arg Lys Val Leu Lys (SEQ ID NO: 68)

GK-20:

Lys Trp Lys Leu Phe Lys Lys Ile Gly Ile Gly Arg Leu Leu Lys Arg Gly Leu Arg Lys Leu Leu Lys (SEQ ID NO: 69)

TABLE 2

MIC of functional analogs of invention peptides GK-19 and GK-20

|  |  | MIC(ug/ml) | |
|---|---|---|---|
|  | Strain | GK-19 | GK-20 |
| G+ | Staphylococcus aureus CMCC26003 | 1.0 | 0.8 |
|  | Bacillus subtilis DB430 | 2 | 2 |
|  | Bacillus pumilus CMCC63202 | 10 | 6 |
|  | Micrococcus lysoleikticus S1.634 | 4 | 2 |
|  | Micrococcus lutea CMCC28001 | 10 | 4 |
| G- | Escherichia coli ATCC8099 | 2 | 8 |
|  | Klebsiella pneumoniae CMCC46117 | 2 | 10 |
|  | B Subacute sclerosing panencephalitis CMCC50094 | 1 | 8 |
|  | Pseudomonas aeruginosa CMCC10104 | 4 | 10 |
| Fungi | Candida albicans ATCC10231 | 16 | 18 |
|  | Saccharomyces cerevisiae ATCC9736 | 12 | 20 |

Lower MIC value means higher antimicrobial activity.

Example 6

In-Vitro Hemolytic Activity

This experiment was to detect the hemolytic activity of the antimicrobial peptides. The references were Cecropin A1 and buforin II, which were solid-phase peptide synthesized by our company. Blood sample was normal human blood.

The test step was shown below:

Human red blood cells was washed by PBS (PBS:35 Mm phosphate buffer/0.15 m NaCl, pH7.0). Suck 100 ul 8% red blood cells suspension to 96-well plate, add 100 ul antimicrobial peptide (including cecropin A1, buforin II, GK-1, GK-2, GK-3) to each well, then incubated at 37° C., after 1 hour, 1500 rpm centrifuged for 5 minutes. Suck 100 ul 4% red blood cells suspension to new 96-well plate, detect the hematoglobin releasing under 414 nm by microplate reader. The negative control was PBS, the positive control was TritonX-100. The result was summarized in table 3:

TABLE 3

Results of hemolytic activity of five antimicrobial peptides

| Concentration of antimicrobial peptide | Hemolytic rate(%) | | | | |
|---|---|---|---|---|---|
| (ug/ml) | cecropin A1 | buforinII | GK-1 | GK-2 | GK-3 |
| 12.5 | 0 | 0 | 0 | 0 | 0 |
| 25 | 0 | 0 | 0 | 0 | 0 |
| 50 | 0 | 0 | 0 | 0 | 0 |
| 100 | 1.2 | 0 | 0.5 | 0.2 | 0.6 |
| 200 | 3 | 0.5 | 0.8 | 1.0 | 1.1 |
| 500 | 10 | 1.7 | 1.5 | 2 | 1.9 |

The number of hemolytic rate in table 3 was smaller, the hemolytic activity of antimicrobial peptide was lower.

Example 7

Acute Toxicity Test in Kunming Mouse

The test was to detect the toxicity to animal of antimicrobial peptides including GK-1, GK-2, GK-3, provided by the invention. The references were Cecropin A1 and buforin II, which were solid-phase peptide synthesized by our company.

60 Kunming mouse, half was female, half was male, weight was 33.5±0.25 g. The dosage of antimicrobial peptide was 1 mg/kg, intramuscular injecting one time per day, consecutive 7 days. We observed the reaction of the mouse under the maximum dosage. The result of the test demonstrated that the mice were normal and no abnormal reaction after 7 days intramuscular injection. It can be concluded that the antimicrobial peptides provided by the invention have no toxicity.

Example 8

Comparison of the Efficacy of Antimicrobial Peptide and Vancomycin Against the *Staphylococcus aureus* Infection in Mice The infection model was *Staphylococcus aureus* infection in the Kunming mouse.

The test step was shown below:

*S. aureus* CMCC26003 was cultured overnight, with moderate agitation, in Veal Infusion broth (Difco) and diluted in broth containing 5% hog gastric mucin (Difco). Male Kunming mice weighing approximately 20 grams were infected intraperitoneally with $10^6$-$10^7$ viable cells. There were 3 mice in each treatment group. Antimicrobial peptide GK-1 was administered intravenously (in 0.1 ml 5% dextrose for injection), within 10 minutes of infection. Vancomycin was administered subcutaneously.

TABLE 4

Efficacy of antimicrobial peptide and vancomycin against *Staphylococcus aureus* infection in mice

| | Inhibitory rate (%) | |
|---|---|---|
| Dose (mg/kg) | GK-1 i.v. | Vancomycin s.c. |
| 0 | 0 | |
| 0.125 | 20 | |
| 0.25 | 100 | |
| 0.5 | 100 | 0 |
| 1.0 | 100 | 40 |
| 2.0 | | 80 |
| 4.0 | | 100 |
| 8.0 | | 100 |

As shown in Table 4, GK-1 protected 100% of the infected mice when administered at a dosage of 0.25 mg/kg intravenously. Vancomycin was 100% effective only at the dosage of 4.5 mg/kg. All of the untreated mice died in less than 24 hours.

This example demonstrated that antimicrobial peptide provided by the invention was effective against *S. aureus* infection in an acute infection model in mice using a highly virulent challenge dose of bacteria.

Example 9

Determination of the Inhibitory Activity Against Tumor Cells

To determine the inhibitory activity of the peptides against tumor cells, a MTT colorimetric assay was performed. Fifty percent inhibitory concentrations of the antimicrobial peptides against tumor cells and normal fibroblasts were determined. Tumor cell K562 (human chronic myeloid leukemia cell), Bcap-37 (human breast cancer cell), QGY-7703 (human hepatocellular carcinoma cell), LOVO colon cancer cell, and mouse NIH-3T3 fibroblast were selected. These cells were provided by the College of Life Sciences, Fudan University. Cells were grown in RPMI1-1640, containing 10% inactivated calf serum. Cells were transferred into the 96-well plate at 2*104 cells/well, and 150 μl was added in each well. After the 96-well plate were incubated overnight at 37, in 5% carbon dioxide, 20 μl diluted peptide solution was added to each well, then incubated for 3 days, 20 μl MTT solution was added to each well, and incubated at 37° C. for 4 hours, 40 μl, 002M HCl solution containing 20% SDS was added to each well to solve the purple crystal, and incubated overnight at 37° C. The absorbance at 570 nm was determined.

TABLE 5

Result of the inhibitory activity against tumor cells (IC50)

| | GK-1 (ug/ml) | GK-2 (ug/ml) | GK-3 (ug/ml) |
|---|---|---|---|
| K562 | 45 | 56 | 13 |
| Bcap-37 | 52 | 47 | 25 |
| QGY-7703 | 38 | 44 | 21 |
| LOVO | 35 | 32 | 31 |
| mouse NIH-3T3 fibroblast | >100 | >100 | >100 |

The results show that the antimicrobial peptides of GK-1, GK-2 and GK-3 all have antitumor activities, and the effect of GK-3 is the best.

What is claimed is:

1. A synthetic antimicrobial peptide comprising an amino acid sequence as set forth in SEQ ID NO:46.

2. The synthetic antimicrobial peptide of claim 1, wherein the amino acid sequence is Lys Trp Lys Leu Phe Lys Lys Ile Gly Ile Gly Arg Leu Leu Lys Arg Gly Leu Arg Lys Leu Leu Lys (SEQ ID NO: 55).

3. The synthetic antimicrobial peptide of claim 2, wherein the Lysine at position 1 is covalently bound to the Lysine at position 23 to form a cyclization derivative.

4. The synthetic antimicrobial peptide of claim 1, wherein the amino acid sequence is Lys Trp Lys Leu Phe Lys Lys Ile Gly Ile Gly Arg Leu Leu Arg Arg Leu Leu Arg Arg Leu Leu Arg (SEQ ID NO: 56).

5. A method for producing a synthetic antimicrobial peptide, comprising:

performing solid-phase chemical synthesis to produce the peptide of claim 1.

6. A method for treating a subject having an infectious disease induced by bacteria and/or fungi, comprising:

administering to the subject the synthetic antimicrobial peptide of claim 1 in an amount effective for treating the infectious disease.

* * * * *

UNITED STATES PATENT AND TRADEMARK OFFICE
CERTIFICATE OF CORRECTION

PATENT NO. : 7,629,438 B2
APPLICATION NO. : 10/526267
DATED : December 8, 2009
INVENTOR(S) : Huang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 718 days.

Signed and Sealed this

Second Day of November, 2010

David J. Kappos
*Director of the United States Patent and Trademark Office*